United States Patent [19]
Bergquist

[11] Patent Number: 5,824,855
[45] Date of Patent: Oct. 20, 1998

[54] SYNTHETIC CORN HYBRID LP53.1-WX

[75] Inventor: Richard R. Bergquist, El Paso, Ill.

[73] Assignee: Optimum Quality Grains, L.L.C., West Des Moines, Iowa

[21] Appl. No.: 829,158

[22] Filed: Mar. 31, 1997

[51] Int. Cl.$^6$ .............................. A01H 5/00; A01H 4/00; C12N 5/04
[52] U.S. Cl. ................ 800/200; 800/250; 800/DIG. 56; 435/412; 435/424; 435/430; 435/430.1; 47/58; 47/DIG. 1
[58] Field of Search ...................................... 800/200, 205, 800/250, 255, DIG. 56; 435/412, 424, 430, 430.1; 47/58, DIG. 1

[56] References Cited

PUBLICATIONS

Aldrich et al., *Modern Crop Production*, 7–13, 46–49 (1982).
Alexander et al., Breeding Special Industrial and Nutritional Types, Chapter from *Corn and Corn Improvement*, Sprague ed., 363–370 (1977).
Allard, *Principles of Plant Breeding*, 166–303 (1960).
Crabb, *The Hybrid Corn Makers*, 229–243 (1991).
Creech et al., Breeding for Industrial and Nutritional Quality in Maize, Chapter in *Maize Breeding and Genetics*, Walden ed., 249–264 (1978).
Dudley et al., Seventy Generations of Selection for Oil and Protein Concentration in Maize, Chapter from *Seventy Generations of Selection for Oil and Protein in the Maize Kernel*, Dudley ed., 181–212 (1974).
Elliott, *Plant Breeding and Cytogenetics*, 260–302 (1958).
Frey, *Plant Breeding II*, 387–395 (1981).
Hayes et al., *Methods of Plant Breeding*, 267–346 (1955).
Orthoeffer et al., Corn Oil; Composition, Processing, and Utilization, Chapter from *Corn: Chemistry and Technology*, Watson et al., ed. 535–551 (1987).
Poehlman, *Breeding Field Crops*, 241–277 (1959).
Stoskopf et al., *Plant Breeding —Theory and Practice*, 1, 185–199, 219–237, 287–325 (1993).
Weber, Lipids of the Kernel, Chapter from *Corn: Chemistry and Technology*, Watson et al., ed., 311–348 (1987).

*Primary Examiner*—Gary Benzion
*Assistant Examiner*—Melissa L. Kimball
*Attorney, Agent, or Firm*—Bullwinkel Partners, Ltd.

[57] ABSTRACT

A synthetic hybrid corn plant having the designation LP53.1-wx, produced by crossing two proprietary Pfister Hybrid Corn Company maize synthetics, LP53.1wx-A and LP53.1wx-B. LP53.1-wx has the unique property of imparting high oil and high protein levels in the grain of certain normal and male sterile hybrids when used as a pollinator. LP53.1-wx is characterized by excellent cold tolerant seedling vigor for rapid emergence in cold soils, and excellent early-season adaptability to nick with early maize hybrids that condition fast dry-down and superior grain quality in the recipient female grain parent. LP53.1-wx also produces a superior quality silage when used to pollinate elite male sterile waxy hybrids, wherein the whole male sterile plant is harvested for silage. This invention thus relates to the synthetic hybrid plants and seeds of LP53.1-wx, i.e., the synthetic hybrid produced by crossing the two aforementioned parental synthetics and the seed thereof, including advanced generation seed, variants, mutants, and modifications of LP53.1-wx.

17 Claims, No Drawings

SYNTHETIC CORN HYBRID LP53.1-WX

FIELD OF THE INVENTION

This invention is in the field of plant breeding. Specifically, this invention relates to a novel synthetic corn hybrid having the designation LP53.1-wx and useful in the proprietary TopCross™ grain production system described in pending U.S. patent applications Ser. Nos. 07/615,839 and 08/464,249 by Bergquist et al.

BACKGROUND OF THE INVENTION

Uses of corn

Corn (*Zea mays* L.) is an important crop used as a human food source, animal feed, and as a raw material in industry. The food uses of corn, in addition to the human consumption of corn kernels, include products of both the dry milling and wet milling industries. The principal products of dry milling include grits, meal and flour. The principal products of wet milling include starch, syrups, and dextrose. A by product of both dry and wet milling is corn oil, which is recovered from corn germ. As animal feed, corn is used primarily as a feedstock for beef cattle, dairy cattle, swine, poultry, and fish.

Industrial uses of corn mainly consist of the use of corn starch produced by wet milling and corn flour produced by dry milling and the whole kernel fermentation for production of food-grade and industrial use ethanol. The industrial applications of corn starch and flour are based on their functional properties, such as viscosity, film formation ability, adhesiveness, absorbent properties and ability to suspend particles. Corn starch and flour are used in the paper and textile industries, and as components in adhesives, building materials, foundry binders, laundry starches, sanitary diapers, seed treatments, explosives, and oil-well muds. Plant parts other than the corn kernels are also used in industry. For example, stalks and husks can be made into paper and wallboard, and corn cobs can be used for fuel and to make charcoal.

Principles of conventional plant breeding

Virtually all of the commercial corn produced in the United States is produced from hybrid seed. The production of hybrid seed first requires the development of elite corn inbred lines that possess good combining ability to produce agronomically superior hybrids. The majority of hybrid seed produced in the United States is of the single cross type, wherein two inbred lines are intermated, or crossed, to produce what is termed an $F_1$ single cross hybrid. The resulting kernels from this intermating are then sold as seed to commercial growers who plant the seed and harvest the second generation, or $F_2$ grain, for use on farm or for commercial sale.

The production of a conventional single cross hybrid seed involves controlling the direction of pollination from one inbred to the other to assure the production of predominantly hybrid (cross pollinated) seed. Typically directed pollination is accomplished by interplanting separate rows of female corn plants with male corn plants. The female corn plants that are male sterile may be produced by genetic mechanisms which render the corn tassel nonfunctional, by cytoplasmic or chemical sterility methods, or by detassling the plants in the field.

The development of corn hybrids requires the development of homozygous inbred lines or uniform synthetic populations of unique heterotic background, the crossing of these lines or synthetic populations, and evaluation of test crosses. Pedigree breeding and recurrent selection breeding programs are used to develop inbred lines and synthetic populations from breeding populations. Breeding various broad-based sources into breeding pools from which new inbred lines or synthetic populations are developed by inbreeding or random mating and selection of desired phenotypes. The new inbreds and/or synthetic lines are crossed with other inbred lines and/or synthetic populations and the hybrids from these crosses are evaluated to determine which have commercial value and agronomic usefulness.

Pedigree breeding starts with the crossing of two genotypes, each of which may have one or more desirable characteristics that is lacking in the other or which complements the other. If the two original genotypes do not provide all of the desired characteristics, other sources can be included during the breeding. In the pedigree breeding method, superior plants are selfed or random mated and the resulting seed selected in successive generations. Pedigree records of ancestry are carefully maintained for each family and ear row selection through succeeding generations. In the succeeding generations, the heterozygous condition of the corn germplasm gives way to homozygous true breeding lines as a result of inbreeding and selection. Typically in the pedigree method of breeding, five or more generations of inbreeding and selection is practiced: $F_1$ to $F_2$; $F_2$ to $F_3$; $F_3$ to $F_4$; $F_4$ to $F_5$, etc.

Backcrossing can be used to improve an inbred line by transferring a specific desirable trait from one inbred or source to another inbred that lacks that trait. This can be accomplished, for example, by first crossing a superior inbred (recurrent parent) to a donor inbred (nonrecurrent parent). The donor inbred carries (donates) the appropriate gene(s) for the desired trait to the next generation. After five or more backcross generations with selection for the desired trait, the inbred will be heterozygous for loci controlling the characteristic being transferred, but will be like the superior parent for most or almost all other genes. The last backcross generation can be selfed to produce a pure breeding progeny for the gene(s) being transferred.

An important consequence of the homozygosity and homogeneity of the inbred lines is that the hybrid between any two inbreds will always be the same. Once the inbreds or synthetics that give the best hybrid have been identified, the hybrid seed can be reproduced indefinitely as long as the homogeneity of the inbred or synthetic parents is maintained.

A synthetic hybrid consists of an array of similar genotypes that were identified from intercross tests and bulked into a random mating population having a desired phenotype. The intercrosses between two different heterotic groups results in the continuous production of a specific synthetic hybrid of desired phenotype.

As previously noted, a single cross hybrid is produced when two unrelated inbred or synthetic lines are crossed to produce the $F_1$ progeny. A three-way cross hybrid is produced from three inbred lines (or synthetics) where two of the inbred lines (or synthetics) are crossed (A×B) and then the resulting $F_1$ hybrid is crossed with the third inbred (or synthetics) (A×B)×C. A double cross hybrid is produced from four inbred lines (or synthetics) by crossing pairs (A×B) and (C×D) and then crossing the two $F_1$ hybrids (A×B)×(C×D).

Much of the hybrid vigor exhibited by $F_1$ hybrids is lost in the next generation ($F_2$). Consequently, seed (grain) from hybrid varieties is not used for planting stock.

The objective of typical plant breeding is to combine in a single variety/hybrid the desirable traits of the parental lines. For field crops such as corn, these desirable traits may include resistance to diseases, insects, herbicide tolerance, and tolerance to heat and drought, reducing time to crop maturity, and improved agronomic quality. With mechanical harvesting of many crops, uniformity of plant characteristics such as germination time and stand establishment, growth rate, and fruit/seed size are also desirable.

The problem with conventional breeding techniques is that there are several grain quality traits, such as high oil content, that cannot readily be combined in a high-yielding single cross hybrid. The present invention, when used as a pollinator, imparts desirable grain quality characteristics, such as high oil content, to the resulting $F_1$ grain without significant loss of yield. This heretofore was not possible because these desirable grain quality characteristics in hybrids usually have been associated with low yield and poor agronomic characteristics.

Synthetic varieties

Corn has male flowers, located on the tassel, and female flowers, located on the ear, of the same plant. Because of this monoecy, corn plants can be bred by both self-pollination and cross-pollination techniques. Corn is self-pollinated if pollen from one flower is transferred to the same or another flower on the same plant. Corn is cross-pollinated if the pollen comes from a flower on a different plant.

Plants that have been self-pollinated and selected for uniform type over many generations become homozygous at almost all gene loci and produce a uniform population of true breeding progeny. Cross pollination between two homozygous lines produces a uniform population of hybrid plants that nevertheless may be heterozygous for many gene loci. A cross between two plants that are each heterozygous for a number of gene loci will produce a population of hybrid plants that differ genetically and will not be uniform.

Natural pollination occurs when wind blows pollen from tassels to silks that protrude from tops of the incipient ears on plants of the same genotype and different genotype, resulting in both self- and cross-pollination. When a population of genotypes are combined from all possible inter-crosses among a number of selected genotypes and are allowed to open pollinate, the result is called a synthetic variety. A synthetic variety is made up of genotypes which previously have been tested for their ability to produce a superior progeny when crossed in all combinations.

Corn plants may be maintained as an outcrossing synthetic population that is much less homogeneous than a self-pollinated group. Every plant in such a group is certain to be heterozygous at many or most loci, and this heterozygosity must either be maintained during a breeding program or restored at the end of the program, if productivity is to be satisfactory. The main requirement in maintaining a synthetic line is that a sufficient number of plants of heterozygous background be maintained to recover the gene frequencies that are desired for the synthetic population so as to prevent genetic drift toward undesired gene frequencies.

The desirability of high oil content grain

The concentration of oil in most varieties of corn ranges from less than 3.0 percent to 4.5 percent at 0% moisture. Embryos of ordinary corn can contain 30 percent oil, while embryos of high oil corn strains can contain as much as 50 percent oil and are much larger in size than ordinary corn embryos.

There are several reasons for wanting to develop a method for growing corn that is high in oil content. First, corn oil is a premium oil and regularly more valuable than starch, the other major component of corn kernels. Second, high oil corn possesses a higher available energy content than ordinary corn, and thus is a more valuable feed for poultry and livestock. In animal feeding trials it has been found that less high oil corn is required per unit of gain than is required with ordinary corn. In addition, high oil corn requires substantially less soybean meal to balance a typical animal diet, and may be used to replace oil containing additives in animal feed.

Additional impetus was given to breeding corn for high oil by the development of wide-line nuclear magnetic resonance spectroscopy (NMR) and near-infrared spectroscopy (NIR) as analytical tools for the nondestructive analysis of bulk or single kernel samples that can be carried out in as little as two seconds. The development of such tools made it much easier and much quicker to determine the oil content of grain, thereby encouraging experimentation in the area of breeding for high oil.

Thus there exists at present a growing market for corn having high oil, increased protein and other special end-use properties which is not met by corn of standard composition. The diverse types of corn available to plant breeders provides a potential for modification of quality and quantity of grain protein, starch, and oil. Corn now can be developed to more precisely meet the specific nutritional requirements of animals or to meet particular industrial needs.

The TopCross™ grain production system

Unfortunately, high oil is a property that cannot readily be achieved in a high yielding single-cross hybrid. This is because oil content, while being a moderately heritable trait, is influenced by a series of oil genes that have additive effects on oil content and occur at a complex of loci in at least eight linkage groups that influence the amount of oil in the grain progeny. Obtaining a hybrid having all or most of these oil genes can take many years of breeding. Further increasing the difficulty of breeding for high oil content is the fact that the grain yield of higher oil hybrids is generally inferior when compared to elite dent corn hybrids.

A method of producing a high yield of corn having high oil content without requiring years of breeding is described in Bergquist et al. U.S. patent application Ser. No. 07/615,839. The primary aspect of this method, known as the TopCross™ grain production system, is the interplanting of a pollinator corn plant possessing the characteristics for significantly increasing oil and protein levels in the resulting grain with a male sterile hybrid corn plant. The resulting grain possesses an oil content much higher than would be expected for self- or cross-pollination of the fertile version of the hybrid corn plant.

In practice, the seed of the pollinator with improved grain quality traits is blended in small amounts with seed of an elite male sterile grain parent hybrid, but with sufficient pollinator seed to permit abundant pollen production for fertilization of the male sterile grain parent hybrid. The relatively low ratio of pollinator seed to male sterile grain parent seed (less than one pollinator plant to every three grain parent plants) takes advantage of the higher grain yield potential of the elite grain parent hybrid while assuring a sufficient population of pollinator plants to pollinate the male sterile grain parent plants.

Need for superior pollinators

Critical to the success of the TopCross™ grain production system is the use of a pollinator capable of enhancing the grain quality traits of the $F_1$ offspring. To obtain such pollinators, the corn breeder must select and develop corn plants that have the traits that result in superior inbred and synthetic parental lines.

The pollinator for the TopCross™ grain production system need not be genetically homozygous (inbred) or even uniform in appearance, and need not be selected for genetic combining ability with female plants. However, the pollinator should have uniform desirable grain quality characteristics, such as high oil, that will influence the grain quality characteristics of the $F_1$ offspring, and the ability to pollinate the female plants. A hybrid obtained by crossing two synthetic populations of different heterotic backgrounds results in a synthetic hybrid with predictable heterozygosity and genetic variability among plants that is particularly useful as a male pollinator in blends with male sterile hybrid grain parents in the TopCross™ grain production system. Some genetic variability is desirable because it extends the flowering period of the pollinator. LP53.1-wx was developed to achieve these characteristics.

Advantages of synthetic hybrids

The use of synthetic hybrids (such as LP53.1-wx) as TopCross™ grain production system pollinators affords a number of advantages over the use of hybrids produced from single crosses. For instance, synthetic hybrids can be developed more rapidly than commercial hybrids. Specifically, the use of a synthetic population can more rapidly establish stability of dominant oil genes, thus by-passing the many generations of inbreeding that is required to produce inbreds for making single cross hybrids.

Second, synthetic hybrids often have excellent vigor comparable to that of commercial hybrids. Inbreds, by contrast, typically lose vigor with each successive generation of inbreeding. This is an important advantage of synthetics because pollinator vigor is critical for ample pollen shed at the time of silking in the TopCross™ grain production system. Synthetic hybrid LP53.1-wx expresses cold vigor in seedling growth stages greater than even most open pollinated synthetic populations.

Third, a synthetic variety, utilizing heterosis in which pollination control is a factor, is more likely to disperse pollen over a longer period of time than a single cross hybrid. The predictable greater variability of synthetic varieties as compared with single crosses permits more flexibility to meet the changing growing conditions typical of field production. In addition, because of the longer flowering period, fewer synthetic pollinators need be developed to be used in blends with many different grain parents.

Fourth, the synthetic hybrid pollinator is more easily produced during periods of heat and drought stress on dryland production than a single-cross hybrid using less vigorous inbred seed stocks. For example, in non-irrigated dryland field tests conducted during 1993 and 1994, production of synthetic hybrid seed remained relatively constant at about 55 bushels per acre despite the fact that rainfall accumulation during the critical months of May, June and July fell from 40.84 cm in 1993 to 13.82 cm in 1994. Over the same period, single cross seed production using inbred seed stocks fell to less than 25 bushels per acre in 1994 from 55 bushels per acre in 1993.

Fifth, the single cross synthetic hybrid pollinator which results from the cross of two parental synthetic populations, A×B, is more quickly produced in a single generation compared to a three-way cross pollinator (A×B)C that requires an additional plant generation to produce the hybrid three-way cross pollinator. For example, the A×B synthetic hybrid is simply produced in a single plant growing generation in the production of LP53.1-wx single-cross synthetic hybrid while the three-way cross synthetic hybrid pollinator would require an additional plant generation to produce the final hybrid (A×B) crossed to the parental C-population to produce a synthetic three-way hybrid cross designated (A×B)C.

SUMMARY

According to the invention, there is provided a novel synthetic corn hybrid, designated LP53.1-wx, that when used to pollinate an elite male sterile hybrid grain parent, produces commercial grain exhibiting improved quality grain traits, including high oil and protein. LP53.1-wx, when used to pollinate male sterile hybrid grain parents that are harvested as whole plants at approximately 50% plant moisture, produces commercial fodder that expresses improved feeding quality traits, including improved efficiency and rate of weight gain. The invention thus relates to the seeds, plants and plant parts of LP53.1-wx; to plants regenerated from tissue culture of the plants or plant parts of LP53.1-wx; and to a method of producing LP53.1-wx by crossing synthetic LP53.1wx-A-Reid and LP53.1wx-B-Lancaster synthetics.

DEFINITIONS

In the description and examples that follow, a number of terms are used. In order to provide a clear and consistent understanding of the specification and claims, including the scope to be given such terms, the following definitions are provided:

Adaptation

The process by which individuals (or parts of individuals) or populations change in form or function to better survive under given environmental conditions. Also the result of this process.

Anthesis

The period or act of flowering.

Backcross

The cross of a hybrid to either one of its parents. The offspring of such a cross is referred to as the backcross generation.

Backcross Method of Breeding

A system of breeding carried out by several generations of backcrossing to one of the parents of a hybrid and subsequent selection. The characteristics of the recurrent parent are retained for the most part, and characteristics from the nonrecurrent parent are added.

Barren Plants

Plants that lack ears, typically measured in number of plants per plot.

Brittle Stalks

This is a measure of the stalk breakage near the time of pollination of the hybrids, and is an indication of whether a hybrid would snap or break at the time of flowering under severe winds.

Bulk Method of Breeding

The growing of segregating generations of a hybrid of self-pollinating crops in a bulk, with or without mass selection, followed by individual plant selection in $F_6$ or later generations.

Cob Score

The cob score is a rating of how well the grain is shelled off the cob and how badly the cob is broken up going through the combine. A high score indicates that the grain shells off of the cob well, and the cob does not break.

Cytoplasmic Inheritance

Transmission of hereditary characters through the cytoplasm as distinct from transmission by genes carried by chromosomes. Detected by differing contribution of male and female parents in reciprocal crosses.

Diallel Cross

The crossing in all possible combinations of a series of genotypes.

Donor Parent

The parent from which one or a few genes are transferred to the recurrent parent in backcross breeding.

Ear Height

The ear height is a measure from the ground to the top developed ear node attachment and is measured in centimeters.

Early Stand Count

This is a measure of the stand establishment in the spring and represents the number of plants that emerge on a per-plot basis for the hybrid.

Embryo

The rudimentary plant in a seed. The embryo arises from the zygote. In high oil corn breeding, increases in oil content are accompanied by increases in embryo size.

Endosperm

The nutritive tissue formed within the embryo sac in seed plants. It commonly arises following the fertilization of the two primary endosperm nuclei of the embryo sac by the two male sperms. In a diploid organism the endosperm is triploid.

Expressivity

The degree of manifestation of a genetic character.

$F_1$

The first generation of a cross.

$F_2$

The second filial generation obtained by self-fertilization or crossing inter se of $F_1$ individuals.

$F_3$

Progeny obtained by self-fertilizing $F_2$ individual. Subsequent generations $F_4$, $F_5$, etc.

GDD Shed

The GDD is the number of growing degree days (GDD) or heat units required for an inbred line or hybrid to reach anthesis or pollen shed from the time of planting. Growing degree days are calculated by the Barger Method, where the heat units for a 24-hour period are:

$$GDD = \frac{(Max. + Min.)}{2} - 50$$

The highest maximum used is 86 degrees F. and the lowest minimum used is 50 degrees F. For each hybrid it takes a certain number of GDDs to reach various stages of plant development. GDDs are a way of measuring plant maturity.

Genotype

The fundamental genetic constitution of an organism.

Grain

Comprises mature corn kernels produced by commercial growers for purposes other than growing or reproducing the species.

Grain Parent

Male sterile, elite hybrid that comprises a large majority of the plants in a TopCross production field.

Grain Parent Seed

Corn seed used to produce grain parent plants.

Grain Quality

This is a 1 to 5 rating for the general quality of the shelled grain as it is harvested based on the color of the harvested grain, any mold on the grain, and any cracked grain. Low scores indicate good grain quality.

Grain Quality Trait

This is any attribute of grain that is of commercial value. Such traits relate to the intermediate or final use of grain and include but are limited to the quantity or quality of oil, protein, starch, pigmentation, and fiber found in corn grain. Such traits also encompass physical attributes of the grain itself, such as grain texture, size, or hardness, among others. Certain of these compositional or physical attributes of grain correlate with functional attributes as well which are of commercial importance, such as susceptibility to breakage and spoilage, among others.

Hybrids (1) The progeny of a cross fertilization between parents belonging to different genotypes. (2) The first generation offspring of a cross between two individuals differing in one or more genes. (3) A hybrid is the result of a cross between two or more components.

Hybrid Vigor

The phenomenon in which the cross of two stocks produce hybrids that show increased vigor-heterosis compared to the parent stocks.

Inbred Lines (1) A line produced by continued inbreeding. In plant breeding a nearly homozygous line usually originating by continued self-fertilization, accompanied by selection. (2) A relatively homozygous line produced by inbreeding and selection.

Male Sterility

A condition in which pollen is absent or non-functional in flowering plants.

MN RM

This represents the Minnesota Relative Maturity Rating (MN RM) for the hybrid and is based on the harvest moisture of the grain relative to a standard set of checks of previously determined MN RM rating. Regression analysis is used to compute this rating.

Moisture

The moisture is the actual percentage moisture of the grain at harvest.

Multiple Genes

Two or more independent pairs of genes which produce complementary or cumulative effects upon a single character of the phenotype.

Pedigree

A record of the ancestry of an individual, family, or strain.

Pedigree Breeding

A system of breeding in which individual plants are selected in the segregating generations from a cross on the basis of their desirability and on the basis of a pedigree record.

Penetrance (1) The proportion of organisms heterozygous for a particular dominant gene or homozygous for a recessive which shows the phenotype under a set of specified environmental conditions; (2) complete penetrance is the situation in which a dominant gene always produces a phenotypic effect or a recessive gene in the homozygous state always produces a detectable effect; (3) the frequency with which a gene produces a recognizable effect in individuals which carry it.

Percent Yield

The percent yield is the yield obtained for the hybrid in terms of percent of the mean for the experiments in which it was grown.

Phenotype (1) Physical or external appearance of an organism as contrasted with its genetic constitution (=genotype); (2) a group of organisms with similar physical or external makeup; (3) the observed character of an individual without reference to its genetic nature.

Plant Height

This is a measure of the height of the hybrid from the ground to the tip of the tassel and is measured in centimeters. The data is given in percentage of mean of the experiments in which the hybrid was grown.

Pollinator

Male fertile corn plants that are used to pollinate male sterile hybrid corn plants.

Population

In genetics, a community of individuals which share a common gene pool. In statistics, a hypothetical and infinitely large series of potential observations among which observations actually made constitute a sample.

Predicted R.M.

Predicted relative maturity is based on the harvest moisture of the grain. The relative maturity rating (R.M.) is based on a known set of checks and utilizes standard linear regression analyses referred to as the Minnesota Relative Maturity Rating System.

Quantitative Character

A character in which variation is continuous so that classification into discrete categories is not possible. Also, a character determined by a series of independent genes which are cumulative in their effect.

Recurrent Parent

Used in backcrosses to refer to the parent to which the first cross and successive backcrossed plants are crossed.

Root Lodging

The percentage of plants that root lodge; i.e., those that lean from the vertical axis at an approximately 30 degree angle or greater would be counted as root lodged.

Seedling Vigor

This is the visual rating (1 to 5) of the amount of vegetative growth after emergence at the seedling stage (approximately five leaves). A higher score indicates better vigor.

Selection Index

The selection index gives a single measure of a hybrids's worth based on information for up to five traits. A corn breeder may utilize his or her own set of traits for the selection index. One of the traits that is almost always included is yield.

Self-fertilization

The fusion of the female egg cell of one individual with a male sperm cell of the same individual.

Sibs

Progeny of the same parents derived from different gametes. Half sibs, progeny with one parent in common.

Single Cross

A cross between two genotypes, usually two genetically different inbred lines or synthetic lines.

Stalk Lodging

This is the percentage of plants that do not stalk lodge, i.e., stalk breakage, as measured by either natural lodging or pushing the stalks and determining the percentage of plants that break off below the ear. This is a relative rating of a hybrid to other hybrids for standability.

Stay Green

Stay green is the measure of plant health near the time of black layer formation (physiological maturity). A low score on a scale of 1 to 5 indicates better late-season plant health.

Synthetic Variety

A variety produced by crossing inter se a number of genotypes selected for good combining ability in all possible hybrid combinations, with subsequent maintenance of the variety by open pollination.

Test Cross

A cross of a double or multiple heterozygote to the corresponding multiple recessive to test for homozygosity or linkage.

Topcross (1) A cross of a hybrid or synthetic or inbred to a multiple heterozygote of opposite corresponding multiple loci to obtain traits observed in the pollen donor parent; (2) a cross between a selection line, clone, etc., and a common pollen parent which may be a variety, inbred line, single cross, etc. The common pollen parent is called the topcross or tester parent. (3) In corn, a topcross is commonly an inbred-variety cross, an outcross of selections, clones, lines, or inbreds, to a common pollen parent.

TC Blend™

A trademark of E. I. DuPont de Nemours and Company, Inc. for a physical seed mixture of pollinator seed and male sterile grain parent seed meeting specific quality criteria.

TopCross™ Grain

The grain which results from the planting of TC Blend™ seed and having improved nutrient composition and grain quality. TopCross™ is trademark of E I. DuPont de Nemours and Company, Inc. for grain produced by the TopCross™ grain production system.

TopCross™ Grain Production System

A method of commercial corn production whereby a low yielding male fertile corn pollinator is blended at 8 to 20 percent of the total seed count with an elite high yielding male sterile hybrid grain parent and allowed to pollinate the male sterile grain parent to produce TopCross™ grain having increased food and feed nutritional value, thus capitalizing on the high yield potential of the male sterile hybrid grain parent while contributing the grain quality traits from the fertile pollinator.

Variety

A subdivision of a species. A group of individuals within a species which are distinct in form or function from other similar arrays of individuals.

Yield (Bushels/Acre)

The yield in bushels/acre is the actual yield of the grain at harvest adjusted to 15.5% moisture.

DETAILED DESCRIPTION OF THE INVENTION

LP53.1-wx is a yellow dent corn, high oil single cross synthetic hybrid having superior agronomic characteristics and the ability to impart desirable grain quality traits to a first generation grain when used as a pollinator in the TopCross™ grain production system.

Synthetic hybrid LP53.1-wx is produced by planting synthetic populations LP53.1wx-A and LP53.1wx-B, allowing one synthetic to pollinate the other, and harvesting the resulting seed. Either synthetic parental population may be used as female parent or the male parent. Preferably, synthetic LP53.1wx-B should be the male of the cross and synthetic LP53.1wx-A should be the female of the cross because of the later flowering growth habit for LP53.1wx-B in hybrid synthetic production. Production planting of the male and female synthetics can be made at the same time due to the fact that male pollen of LP53.1wx-B is shed approximately four days later than when the female silks of LP53.1wx-A are receptive to the pollen.

LP53.1wx-A and LP53.1wx-B were produced by conducting a series of crosses, selfings and backcrosses beginning with the crossing of B73 and NC282 with ASKC28 (for LP53.1wx-A) and the crossing of LH85, LH162, ITR-1 and F2 with ASKC28 (for LP53.1wx-B.

When produced according to the method disclosed herein, both LP53.1wx-A and LP531.wx-B breed true, that is, produce an LP53.1-wx synthetic hybrid that is both reproducible and usable as a high oil TopCross™ pollinator.

CHARACTERISTICS

Synthetic corn hybrid LP53.1-wx most closely resembles maize synthetics ASKC28, ASKC20 and UHO in characteristics of plant type, ear type, kernel type and usage, but LP53.1-wx is considerably earlier in maturity and expresses similar grain test weight to ASKC28 with waxy grain and dent phenotype.

LP53.1-wx synthetic hybrid has the following characteristics as presented in Table 1:

TABLE 1

SYNTHETIC HYBRID LP53.1-wx DESCRIPTION INFORMATION

| | |
|---|---|
| Type: | Dent/High Oil |
| Region Best Adapted: | Most Northern Regions of Cornbelt |
| A. Maturity: | Zone 0 |
| Synthetic Corn Hybrid: | LP53.1-wx |
| Heat Units from Emergence to Shed: | 1087.0 GDD |
| Heat Units from Emergence to Silk: | 1174.0 GDD |
| Heat Units from 50% Silk to 25% Kernel Moisture: | 1452.0 GDD |
| Heat Units from Emergence to 25% Kernel Moisture: | 2626.0 GDD |
| No. Reps.: | 8 |
| Heat Units* = | [(Max. Temp. (<86 Degrees F.) + Min. Temp. (>50 Degrees F.)) / 2]− 50 |
| | *If Max. Temp. is greater than 86 degrees Fahrenheit, then 86 is used and if Min. Temp. is less than 50, then 50 is used. Heat units accumulated daily and can not be less than 0. |
| B. Plant Characteristics: | |
| Height (to tassel tip): | 207 cm |
| Length of Top Ear Internode: | 14 cm |
| Number of Ears per Stalk: | 1–2, slight two-ear tendency |
| Ear Height (to base of top ear): | 84 cm |
| Number of Tillers: | None |
| Cytoplasm Type: | Normal |
| Brace Root Color: | Green |
| Number of Brace Root Nodes: | 1 |
| Number of Brace Roots: | 5.6 |
| C. Leaf: | |
| Color: | Green |
| Stalk Color: | Green |
| Angle from Stalk: | 61 Degrees |
| Marginal Waves (number): | 2–3, few |
| Number of Leaves (mature plants): | 11 |
| Sheath Pubescence: | Smooth, pubescence absent |
| Longitudinal Creases: | Absent |
| Length (Ear node leaf): | 79 cm |
| Width (widest point, ear node leaf): | 8 cm |
| Coleoptile Sheath Color: | Green |
| D. Tassel: | |
| Number Lateral Branches: | 11 |
| Branch Angle from central spike: | 60 degrees |
| Length (from flag leaf): | 51 cm |
| Peduncle Length (flag leaf to basal branches): | 7 cm |
| Anther Color: | Pale green, was segregating for pink anther color but heterozygous for pale green |
| Glume Color: | Pale green |
| E. Ear (Husked Ear Data Except When Stated Otherwise): | |
| Length: | 19 cm |
| Weight (dried to 15.5% grain moisture): | 147.7 gm |
| Mid-point Diameter: | 4 cm |
| Silk Color (at silking): | Pale green |
| Husk Extension (Harvest stage): | Short, 5.0 cm |
| Husk Leaf (number): | 5 |
| Husk Leaf Length: | 5 cm |
| Number of Husks: | 11 |
| Taper of Ear: | Average taper |
| Position at Dry Husk Stage: | Upright |
| Kernel Rows: | 18; Distinct, straight, segregating 14 to 22 rows |
| Husk Color (fresh): | Light green |
| Husk Color (dry): | Buff |

TABLE 1-continued

SYNTHETIC HYBRID LP53.1-wx DESCRIPTION INFORMATION

| | |
|---|---|
| Shank Length: | 12 cm long |
| Shank (No. of internodes): | 9 |
| Drying Time (unhusked ear): | Average |
| Husk Length: | 23 cm |
| Husk Width: | 13 cm |
| Husk Area: | 299 cm2 |
| F. Kernel (dried, size from ear mid-point) | |
| Length: | 11 mm |
| Width: | 6 mm |
| Thickness: | 3 mm |
| Shape Grade (% rounds): | 18%(±3%) based on parent test |
| Pericarp Color: | Colorless |
| Aleurone Color: | Homozygous; yellow |
| Cap Color: | Yellow |
| Endosperm Color: | Yellow |
| Endosperm Starch Type: | Normal starch |
| Gm Wt/100 Seeds (unsized): | 16 gm |
| Test Weight: | 58 lbs./bu. |
| Percent Oil: | 20.75 percent |
| Percent Protein: | 15.75 percent |
| Percent Starch: | 47.7 percent |
| G. Cob (dried, size from ear mid-point): | |
| Diameter at mid-point: | 25 mm |
| Strength: | Strong |
| Color: | Red, segregating for white and red cob color but was heterozygous for red. |
| H. Diseases: | |
| Northern Leaf Blight: | Intermediate |
| Goss's Bacterial Wilt: | Intermediate |
| Southern Corn Leaf Blight: | Susceptible |
| Heat Smut: | Susceptible |
| Common Smut: | Resistant |
| Stewart's Bacterial Wilt: | Intermediate |
| Corn Lethal Necrosis: | Susceptible |
| Northern Leaf Spot: | Intermediate |
| Common Northern Rust: | Intermediate |
| Southern Rust: | Susceptible |
| Eye Spot: | Intermediate |
| Gray Leaf Spot: | Susceptible |
| Fusarium Ear Rot: | Resistant |
| Fusarium Stalk Rot: | Intermediate |
| Diplodia Ear Rot: | Susceptible |
| Diplodia Stalk Rot: | Intermediate |
| MDMV: | Susceptible |
| Stunt: | Susceptible |
| Stay Green: | Intermediate |
| I. Insects: | |
| European Corn Borer: | Susceptible |
| J. Variety most closely resembling: | |
| Character | Synthetic and/or Hybrid, Inbred |
| Maturity | W117, Pfister X571 |
| Plant Type | ASKC28, UHO, ASKC20 |
| Ear Type | ASKC28, UHO, ASKC20 |
| Kernel Type | UHO, ASKC20 |
| Usage | ASKC28, UHO, ASKC20 |

LP53.1-wx is adapted over a wide area of the northern corn belt and can be used advantageously in seed blends with male sterile hybrids from approximately 96–105 relative maturity based on the Minnesota Relative Maturity Rating System for harvest moisture of the grain. LP53.1-wx cold test vigor was excellent in laboratory tests, exhibiting 92% emergence compared to 90% emergence for ASKC20, 92% emergence for UHOC3, and 83% emergence for ASKC28 (LSD=8.5%; C.V.=5.6% at 0.05 and Stand. Dev.=4.4). Kernel size-out is also very good for LP53.1-wx, with approximately 82 percent of the kernels falling in the medium flat category.

Although LP53.1-wx's primary use would be as a pollinator in the TopCross™ grain production system with blends of early maturing corn hybrid male sterile grain parents, it is also an acceptable male to be crossed to later maturing full season high oil pollinators to develop medium maturity pollinators for expanding the use of its genetics to fuller season maturity grain parents.

Pollen production is good with LP53.1-wx. Under extreme heat and drought stress, LP53.1-wx may top fire and have some tassel blasting (necrosis of top leaves and tassel, respectively). It sheds pollen for approximately sixteen days and should be planted in 8 to 20 percent blends to ensure adequate pollen in commercial production of TopCross™ grain where it is used as a male pollinator.

LP53.1-wx has shown uniformity and stability within the limits of environmental influence for all traits as described in Table 1. LP53.1-wx has expressed segregation for red and white cob color because of the genetic differences of LP53.1wx-A and LP53.1wx-B synthetic parent populations. LP53.1-wx is a synthetic hybrid that has been maintained by hand and cross pollination in isolated fields with continued observation of high oil for uniformity of dominant high oil genetics. Although segregating for cob color, glume color and plant height in test crosses, LP53.1-wx synthetic has consistently expressed high oil across different environments.

LP53.1-wx is an early flowering synthetic hybrid, broadly adapted to the corn growing areas of the Northern United States and Southern Canada. LP53.1-wx has high oil and excellent cold soil seedling vigor that conditions low grain moisture, high oil and high protein in the grain of the male sterile hybrid grain parent.

BENEFITS OF LP53.1-wx AS A POLLINATOR

In field tests of the TopCross™ grain production system using LP53.1-wx as the pollinator and a male sterile hybrid grain parent, plants of both varieties were allowed to grow unmolested to maturity. Both varieties were allowed to continue to grow and natural cross-pollination occurred by the action of wind as is normal in most grasses, including corn (i.e., excluding wheat). Of course, only pollen from the male parent synthetic hybrid, LP53.1-wx, was available for pollination of the male sterile hybrid grain parent; the tassels, or pollen bearing flowering parts, of the grain parent having been rendered sterile by genetic/cytoplasmic mechanisms.

The fields where high oil TopCross™ grain was produced were well isolated from other corn fields to prevent any accidental contamination with ambient pollen. Such isolation techniques may be accomplished by timed delay with other hybrid corn production fields or by using a space distance pattern of more than 70 m from normal corn, well known to those skilled in the art of the seed corn industry.

Both varieties comprising the corn seed blend were allowed to continue to grow and be harvested. The ears harvested from the male sterile grain parent expressed the higher grain yield potential of the elite male sterile grain parent and the high oil and protein of the pollen parent. The grain from the male parent variety ears can also be harvested along with the grain of male sterile grain parent for high oil corn use.

Because the same oil source (i.e. ASKC28) was used in the development of the LP53.1wx-A-Reid and LP53.1wx-B-Lancaster populations, only modest heterotic effects for yield were expressed in LP53.1-wx. The low grain yields expected from synthetic hybrid LP53.1-wx pollinator dictated the need for a low percent of pollinator in the pollinator-grain parent seed blend so as to recover the grain quality traits of the pollinator, but a high enough percent to produce sufficient pollen to maintain the higher yield potential of the elite male sterile grain parent hybrid.

The field tests indicated that LP53.1-wx induces superior grain quality characteristics to TopCross™ grain of the male sterile hybrid grain parent as a result of being pollinated by LP53.1-wx. That is to say, the grain quality traits and high oil characteristics of LP53.1-wx were transferred to the grain of the male sterile grain parent.

EXAMPLES

In the examples and tables that follow, the characteristics of TopCross™ grain (grain yield, moisture content, oil content, protein content and test weight) produced using LP53.1-wx as a pollinator are provided.

First year (1995) strip test trials were conducted at El Paso and Genesco, Ill.; Cedar Falls, Iowa; Janesville, Wis. and Dennison, Minn., comparing the characteristics of grain from a sterile hybrid grain parent pollinated by LP53.1-wx with the characteristics of grain produced from grow outs of the same hybrids in their fertile state. These results are presented in Table 2.

TABLE 2

1995 LP53.1-wx TopCross Strip Test Results - Five Locations

| Hybrid GP (Grain Parent) and Location | Grain Yield-Bu/A. | | | Moisture Percent | | | Oil Percent | | | Protein Percent | | | Test Weight (Lbs./Bu.) | | |
|---|---|---|---|---|---|---|---|---|---|---|---|---|---|---|---|
| | Top-Cross | % of GP | Hybrid Self | Top-Cross | % of GP | Hybrid Self | Top-Cross | % of GP | Hybrid Self | Top-Cross | % of GP | Hybrid Self | Top-Cross | % of GP | Hybrid Self |
| Pfister Hybrid X577-Sdms + LP53.1-wx | | | | | | | | | | | | | | | |
| El Paso, IL | 118.0 | 100 | 117.9 | 16.9 | 90 | 18.8 | 10.20 | 209 | 4.86 | 10.5 | 115 | 9.1 | 51.7 | 91 | 56.7 |
| Geneseo, IL | 145.2 | 90 | 161.9 | 15.0 | 103 | 14.5 | 10.30 | 227 | 4.53 | 10.5 | 113 | 9.3 | 52.1 | 90 | 57.6 |
| Cedar Falls, IA | 88.8 | 71 | 124.5 | 16.7 | 129 | 12.9 | 8.70 | 189 | 4.61 | 10.1 | 111 | 9.1 | 47.8 | 90 | 53.2 |
| Janesville, WI | 61.4 | 74 | 83.0 | 17.0 | 105 | 16.2 | 7.83 | 164 | 4.78 | 7.1 | 101 | 7.0 | 48.9 | 93 | 52.7 |
| Dennison, MN-I | 100.9 | 73 | 137.6 | 17.0 | 105 | 16.2 | 7.90 | 155 | 5.11 | 9.7 | 106 | 9.1 | 52.8 | 92 | 57.4 |
| Dennison, MN-II | 113.4 | 87 | 130.5 | 21.6 | 106 | 20.4 | 8.40 | 199 | 4.21 | 10.2 | 111 | 9.2 | 50.3 | 89 | 56.3 |
| Mean | 104.6 | 83 | 125.9 | 17.4 | 105 | 16.5 | 8.89 | 190 | 4.68 | 9.7 | 110 | 8.8 | 50.6 | 91 | 55.6 |

Second year (1996) strip test trials were conducted in El Paso and Milledgeville, Ill.; Remsen, Iowa and Leipsic, Ohio, comparing the characteristics of grain from various Pfister hybrids rendered male sterile and pollinated by LP53.1-wx with the characteristics of grain produced from grow outs of the same Pfister hybrids in their fertile state. The hybrids used were Pfister hybrids X571, 2020, 2320, 3034, 1571, X692, X591, X687 and X686. These results are presented in Table 3.

TABLE 3

1996 LP53.1-wx TopCross Strip Test Results

| Hybrid GP (Grain Parent) and Location | Grain Yield-Bu/A. | | | Moisture Percent | | | Oil Percent | | | Protein Percent | | | Test Weight (Lbs./Bu.) | | |
|---|---|---|---|---|---|---|---|---|---|---|---|---|---|---|---|
| | Top-Cross | % of GP | Hybrid Self | Top-Cross | % of GP | Hybrid Self | Top-Cross | % of GP | Hybrid Self | Top-Cross | % of GP | Hybrid Self | Top-Cross | % of GP | Hybrid Self |
| Pfister Hybrid X571Sdms + LP53.1-wx | | | | | | | | | | | | | | | |
| Mean* | 136.8 | 90 | 153.6 | 22.4 | 101 | 22.5 | 8.5 | 187 | 4.6 | 9.0 | 118 | 7.6 | 54.6 | 100 | 54.5 |
| Pfister Hybrid 2020Sdms + LP53.1-wx | | | | | | | | | | | | | | | |
| Mean* | 149.9 | 97 | 155.4 | 24.0 | 104 | 23.0 | 8.8 | 199 | 4.5 | 8.7 | 116 | 7.5 | 48.6 | 92 | 53.2 |
| Pfister Hybrid 2320Sdms + LP53.1-wx | | | | | | | | | | | | | | | |
| Mean* | 152.0 | 97 | 155.9 | 24.5 | 107 | 23.1 | 8.2 | 182 | 4.6 | 9.7 | 126 | 7.7 | 53.4 | 96 | 55.6 |
| Pfister Hybrid 3034Sdms + LP53.1-wx | | | | | | | | | | | | | | | |
| Mean* | 155.3 | 94 | 168.6 | 29.1 | 123 | 23.6 | 8.0 | 175 | 4.6 | 8.7 | 116 | 7.5 | 48.4 | 80 | 52.9 |
| Pfister Hybrid 1571Sdms + LP53.1-wx | | | | | | | | | | | | | | | |
| Mean* | 147.3 | 95 | 155.6 | 25.0 | 112 | 22.7 | 8.4 | 184 | 4.6 | 9.0 | 117 | 7.7 | 51.8 | 95 | 54.8 |
| Pfister Hybrid X692Sdms + LP53.1-wx | | | | | | | | | | | | | | | |
| El Paso, II | 131.1 | 84 | 155.3 | 22.1 | 119 | 18.5 | 8.3 | 193 | 4.3 | 8.8 | 103 | 8.5 | 53.1 | 92 | 57.9 |
| Pfister Hybrid X687Sdms + LP53.1wx | | | | | | | | | | | | | | | |
| El Paso, IL | 113.3 | 100 | 113.8 | 16.9 | 105 | 16.1 | 8.4 | 183 | 4.6 | 9.4 | 100 | 9.4 | 54.0 | 95 | 57.1 |
| Pfister Hybrid X688Sdms + LP53.1wx | | | | | | | | | | | | | | | |
| El Paso, IL | 155.8 | 111 | 140.7 | 18.3 | 117 | 15.7 | 8.2 | 187 | 4.5 | 9.1 | 105 | 8.7 | 53.7 | 93 | 57.5 |
| Overall Mean | 146.7 | 95 | 155.5 | 24.4 | 110 | 22.3 | 8.3 | 187 | 4.5 | 9.1 | 113 | 8.1 | 51.6 | 93 | 54.5 |

*Four locations.

Data obtained from the first and second year strip tests included the following:

"Grain yield", expressed in bushels per acre for both the grain produced by the pollination of the male sterile hybrid by LP53.1-wx and for the fertile hybrid. Grain yield from the male sterile/LP53.1-wx seed blend is also expressed as a percent of the yield from the fertile grain parent yield (% of GP).

"Moisture Percent" (for grain produced from the seed blend and from the fertile grain parent), expressed as a percentage of total kernel weight. Relative grain moisture was determined by distillation on a Brown-Duvel moisture tester manufactured by the Seed Trade Reporting Bureau, Chicago, Ill. Electronic moisture testers were calibrated against the moisture determinations of the Brown-Duvel moisture tester in field harvest tests.

"Oil Percent", the content of oil in the grain at harvest, expressed as a percent of total kernel weight. Oil percent was determined by NIR on a dry matter basis (0% moisture).

"Protein Percent", expressed as a percentage of protein in the grain on a dry matter basis as determined by NIR.

"Test Weight", expressed as the weight of the grain in pounds for a given volume (bushel) adjusted for percent moisture.

Yield Comparison

In the first year (1995) strip test trials (Table 2), blends of 8–9 percent pollinator seed and 91–92 percent male sterile hybrid seed were planted and grown to maturity. Grain from both the male sterile hybrid plants and the pollinator plants were harvested. The mean average yield of grain produced by the pollination of the male sterile hybrid by LP53.1-wx was 83% of the mean average yield of grain from the fertile grain parent alone. In second year (1996) trials (Table 3), grain yield from blends of 8–9 percent pollinator and 91–92 percent male sterile grain parent averaged 95% of the yield from the fertile grain parent alone in 23 strip tests.

Moisture Of TopCross™ Grain

Conventional high oil hybrids traditionally express higher grain moisture at harvest and are slower to dry down than lower-oil dent hybrids of the same maturity. To test this concept of higher moisture associated with higher oil content of grain, comparisons were made of moisture at harvest of grain resulting from the pollination by LP53.1-wx of male sterile Pfister hybrids and grain resulting from the self pollination of the comparable fertile Pfister hybrids.

In first year trials (Table 2), the mean grain moisture percent at harvest from the sterile grain parent hybrids pollinated by LP53.1-wx (17.4%) was indeed higher than the mean grain moisture percent from the fertile grain parent hybrids alone (16.5%), thus supporting the conventional theory regarding the relationship between oil content and grain moisture.

In second year trials (Table 3), mean grain moisture percent at harvest from the sterile grain parent hybrids pollinated by LP53.1-wx (24.4%) was also higher than the mean grain moisture percent from the fertile grain parent hybrids alone (22.3), also tending to support the theory that higher moisture is associated with higher oil.

Oil Content Of TopCross™ Grain

Comparisons of the oil content of TopCross™ grain were made against the oil content of grain from fertile hybrids.

The oil contents of grain produced in first year (1995) strip tests of Pfister male sterile hybrids X571-Sdms Pollinated by LP53.1-wx are presented in Table 2. Comparisons of these oil contents to the oil contents of the grain from the fertile checks of these hybrids in tests made at El Paso and Geneseo, Ill.; Cedar Falls, Iowa; Janesville, Wis. and Dennison, Minn. revealed about a 4% absolute increase in oil (8.89% compared to 4.68% for Pfister Hybrid X571.

In second year (1996) comparisons (Table 3), the mean oil content of grain produced by male sterile Pfister Hybrids X571, 2020, 2320, 3034, 1571, X692, X687 and X688 pollinated by LP53.1-wx was 84 percent higher than the mean oil content of grain produced from the self pollination of the fertile hybrid alone (8.3 percent compared to 4.5 percent)

Protein Content

In the first and second year strip tests across eight locations, protein content of the TopCross™ grain (i.e., the grain resulting from the pollination of the male sterile hybrid by LP53.1-wx) was compared to the protein content of grain produced from open pollinated fertile hybrid checks. Analysis of mean protein content indicated that LP53.1-wx significantly increased protein in the TopCross™ grain compared to the grain from the fertile grain parent check.

For example, in first year strip testing (Table 2), the mean protein level of grain produced by the pollination of Pfister Hybrid X577 by LP53.1-wx (9.7%) was 110 percent of the mean protein level in grain produced by the self pollination of fertile X577 (8.8%). In second year strip tests (Table 3), the mean protein level from grain produced by the pollination of eight Pfister hybrids by LP53.1-wx (9.1%) was 113 percent of the mean protein level in grain produced by the self pollination of the fertile hybrids (8.1%).

Test Weight

Test weight of grain is a function of kernel density. In first year strip tests, comparisons of the test weight of TopCross™ grain resulting from the pollination by LP53.1-wx of male sterile Pfister Hybrid X577 was made against the test weight of grain resulting from the self pollination of the comparable fertile hybrids. As shown in Table 2, the mean test weight of TopCross grain across five locations was 50.6 lbs./bu., or 91% of the mean test weight of the selfed X571 (55.6 lbs./bu.). In second year strip tests, the mean test weight of TopCross grain produced by the pollination of eight Pfister hybrids by LP53.1-wx was 51.6 lbs./bu., or 93% of the mean test weight of the selfed hybrids.

LP53.1-wx is a soft starch, low density, high oil TopCross pollinator that was derived from ASKC28 that also conditions the expression of soft starch and low test weight in TopCross grain produced on the elite male sterile hybrid grain parent. The addition of soft starch to the endosperm thus permits a greater expansion of the embryo in the seed and therefore an accompanying increase in oil content as the result of the larger embryo being developed.

Tassel-Silk Synchronization

The success of the TopCross™ grain production system relies in large part on the synchronization of pollen shed from the pollinator with the extrusion of silks from the male sterile grain parent hybrid, which is termed nicking.

Table 4 provides data on the pollen shedding and silk extrusion dates for LP53.1-wx in 1995 tests. As shown in the table, the pollination period of LP53.1-wx extended over 16 days (July 13 to July 28) with the 50% shedding date occurring July 17, which resulted from an accumulation of 1219.5 GDD. In the same experiment, the 50% silk extrusion date for X571 was July 15, which resulted from an accumulation of 1168.0 GDD. This difference was interpreted as approximately two calendar days. Since pollen production typically extends over 16 days with peak pollen production occurring about 8 days after initial pollen shed, this difference is acceptable.

TABLE 4

Frequency Distribution of Pollen Shedding Period and Frequency Distribution of Silk Extrusion Period for LP.53.1-wx (1995)

| | \multicolumn{9}{c}{Date and Percent of Population} | | | | | | | | |
|---|---|---|---|---|---|---|---|---|---|
| | July 13 | July 14 | July 15 | July 16 | July 17 | July 18 | July 19 | July 20 | July 21 |
| Starting Shedding Date | 0.81 | 0.81 | 15.94 | 10.81 | 30.81 | 15.13 | 6.49 | 5.68 | 4.86 |
| Last Shedding Date | 0.00 | 0.00 | 0.81 | 0.11 | 27.57 | 8.92 | 3.51 | 15.68 | 10.00 |
| Silk Extrusion Date | 0.00 | 0.00 | 2.43 | 0.27 | 17.30 | 8.65 | 7.03 | 7.30 | 11.89 |

| | July 22 | July 23 | July 24 | July 25 | July 26 | July 27 | July 28 | Dead | Plants Observed |
|---|---|---|---|---|---|---|---|---|---|
| Starting Shedding Date | 1.89 | 0.27 | 1.89 | 0.54 | 0.27 | 0.81 | 0.81 | 2.16 | 370 |
| Last Shedding Date | 11.89 | 1.35 | 4.32 | 7.57 | 1.62 | 2.70 | 2.43 | 1.62 | 370 |
| Silk Extrusion Date | 5.95 | 2.70 | 6.49 | 3.78 | 4.59 | 1.89 | 1.89 | 17.83 | 370 |

Silage

When used to pollinate certain elite male sterile grain parents, LP53.1-wx conditions the expression of a soft starch, low test weight grain. When harvested as whole plants, the grain parent plants make excellent silage. Nutritional values of silage from Pfister Hybrid X571-Sdms pollinated by LP53.1-wx compared to silage from the fertile normal grain parent type hybrid X571 are presented in Table 5 from two experiments. Silage evaluations were provided by the DuPont Optimum Quality Grain Laboratory, Des Moines, Iowa.

TABLE 5

High Oil TopCross Silage Evaluation - Percent Dry Weight Basis (1995) Four Locations

| Hybrid | Protein | Fat | NEL* M Cal/lb. | TDN* |
|---|---|---|---|---|
| Experiment 1 | | | | |
| Pfister X571 + LP53.1-wx | 8.1 | 6.97 | 0.74 | 71.6 |
| Pfister X571 | 7.5 | 2.06 | 0.70 | 68.1 |
| Experiment 2 | | | | |
| Pfister X571 + LP53.1-wx | 10.7 | 5.16 | 0.72 | 69.3 |
| Pfister X571 | 10.4 | 2.20 | 0.69 | 66.6 |

*NEL = Net Energy for Lactation; TDN = Total Digestible Nutrients

In the first experiment, compared to silage from the fertile normal grain parent alone, corn silage from the LP53.1-wx pollination provided greater total digestible nutrients (71.6 versus 68.1) and greater net energy for lactation (0.74M Cal/lb. versus 0.70M Cal/lb.). Higher NEL and TDN permits greater flexibility in animal feed formulation and increases the productivity per acre for each cow. Protein content of TopCross silage was 0.6% higher on an absolute basis (8.1 versus 7.5) than silage produced from self pollinated fertile hybrid X571. Fat, a function of oil content, was much higher in the TopCross silage.

In experiment 2, the results were similar. NEL, TDL and protein values for the TopCross silage were higher that those for the self pollinated X571 hybrid. As expected, fat was also much higher in the TopCross silage.

DEPOSIT INFORMATION

Applicant has made available to the public without restriction a deposit of at least 2500 seeds of synthetic hybrid LP53.1-wx with the American Type Culture Collection (ATCC), Rockville, Md. 20852, ATCC Deposit No. 97870. Synthetic parental seed stocks of LP53.1wx-A and LP53.1wx-B have also been made available to the public without restriction from a deposit of at least 2500 seeds of each synthetic population with the American Type Culture Collection (ATCC) under Deposit No. 97886 for LP53.1wx-A and No. 97873 for LP53.1wx-B.

The seeds deposited with the ATCC are taken from the same deposits maintained by Pfister Hybrid Corn Company, Box 187, 187 North Fayette Street, El Paso, Ill. 61738, since prior to the filing date of this application. The deposits will be maintained in the ATCC depository, which is a public depository, for a period of 30 years, or 5 years after the most recent request, or for the effective life of the patent, whichever is longer, and will be replaced if a deposit becomes nonviable during that period.

ASKC28 has been previously deposited with the ATCC. NC282, B73, ITR-1, F2, LH85 and LH162 are publicly available maize materials.

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

What is claimed is:

1. A synthetic hybrid corn seed designated LP53.1-wx and having ATCC accession No. 97870.

2. A synthetic hybrid corn plant or its parts produced by the seed of claim 1.

3. Corn plants regenerated from tissue culture of the synthetic hybrid corn plant of claim 2.

4. Pollen of the synthetic hybrid corn plant of claim 2.

5. Tissue culture according to claim 3 comprising regenerable cells of a plant part selected from the group consisting of meristematic tissue, anthers, leaves, embryos, protoplasts, and pollen.

6. A corn plant regenerated from regenerable cells of a tissue culture according to claim 5.

7. A synthetic hybrid corn plant having all the phenotypic, genotypic and physiological characteristics of the seed of claim 1.

8. A method for producing a synthetic hybrid corn seed having the designation LP53.1-wx and having ATCC accession No. 97870 comprising the steps of:

a) planting in pollinating proximity seeds of corn synthetic lines LP53.1wx-A (ATCC accession No. 97886) and LP53.1wx-B (ATCC accession No. 97873);

b) cultivating corn plants resulting from the planting until the time of flowering;

c) emasculating the flowers of the plants of either synthetic line LP53.1wx-A or LP53.1wx-B;

d) allowing natural cross pollination to occur between the synthetic lines; and e) harvesting seeds produced on the emasculated plants of the synthetic line.

9. A synthetic hybrid corn plant designated LP53.1-wx and seed thereof produced by crossing a synthetic corn plant according to claim 2 and having one half the nuclear genotype of the synthetic corn plant of claim 2.

10. Corn grain produced by the process of:

(a) planting, in pollinating proximity, seeds of synthetic hybrid corn plant LP53.1-wx and having ATCC accession No. 97870 and seeds of a male sterile corn hybrid;

(b) cultivating corn plants resulting from the planting;

(c) allowing the LP53.1-wx corn plants to pollinate the male sterile hybrid corn plants;

(d) harvesting the resulting corn grain from all plants.

11. The method of claim 10 wherein the male sterile corn hybrid is rendered male sterile by genetic methods.

12. The method of claim 10 wherein the male sterile corn hybrid is rendered male sterile by cytoplasmic methods.

13. The method of claim 10 wherein the male sterile corn hybrid is rendered male sterile by chemical sterility methods.

14. The method of claim 10 wherein seeds of a male sterile corn hybrid have a waxy grain background.

15. Synthetic corn seed designated LP53.1wx-A and having an ATCC Accession No. 97886.

16. Synthetic corn seed designated LP53.1wx-B and having an ATCC Accession No. 97873.

17. A seed blend comprising a mixture of male sterile hybrid corn seed and the synthetic hybrid corn seed of claim 1.

* * * * *

UNITED STATES PATENT AND TRADEMARK OFFICE
CERTIFICATE OF CORRECTION

PATENT NO. : 5,824,855
DATED : October 20, 1998
INVENTOR(S) : Richard R. Bergquist It is certified that error appears in the above-indentified patent and that said Letters Patent is hereby corrected as shown below:

In claim 9, delete "designated LP53.1-wx", and after "claim 2" (first occurrence) delete "and" and add -- with another, different corn line, the resulting progeny --.

Signed and Sealed this

Twentieth Day of June, 2000

*Attest:*

Q. TODD DICKINSON

*Attesting Officer*    Director of Patents and Trademarks